United States Patent [19]

Devonec

[11] Patent Number: 5,391,196
[45] Date of Patent: Feb. 21, 1995

[54] METHOD FOR THERAPEUTIC TREATMENT OF AN OBSTRUCTED NATURAL CANAL

[76] Inventor: Marian Devonec, 81 avenue des Balmes, 01700 Miribel, France

[21] Appl. No.: 78,025

[22] Filed: Jun. 18, 1993

[51] Int. Cl.$^6$ .............................................. A61N 1/00
[52] U.S. Cl. ...................................... 607/96; 607/97; 607/101; 607/113; 623/12
[58] Field of Search ................... 607/89, 97, 101, 107, 607/154, 156, 96, 113, 104, 105; 606/191, 197; 600/3; 623/8, 11, 12

[56] References Cited

U.S. PATENT DOCUMENTS

| | | | |
|---|---|---|---|
| 5,045,056 | 9/1991 | Behl | 607/113 |
| 5,159,925 | 11/1992 | Newwirsh et al. | 607/105 |
| 5,192,307 | 3/1993 | Wall | 623/12 |
| 5,269,802 | 12/1993 | Garber | 623/12 |

FOREIGN PATENT DOCUMENTS 0370890  5/1990  European Pat. Off.

Primary Examiner—Lee S. Cohen
Assistant Examiner—Brian M. Green
Attorney, Agent, or Firm—Oliff & Berridge

[57] ABSTRACT

An obstructed canal of the human or animal body delimited by a wall is treated by: (a) selectively damaging extrinsic tissue by introducing a controlled dose of ionizing or non-ionizing treatment energy in order to necrose at least a part of the tissue; (b) fitting a prosthesis into the natural canal, the prosthesis including a tubular element biologically compatible with the wall, exerting on the latter a centrifugal compression, and optionally imparting a posture, and defining an open and permanent passage in the natural canal; (c) permitting the extrinsic tissue to heal on and around the prosthesis; and (d), after healing of the extrinsic tissue, extracting the prosthesis from the natural canal to obtain in the latter a definitive passage modeled on the external dimensions of the prosthesis.

9 Claims, 2 Drawing Sheets

METHOD FOR THERAPEUTIC TREATMENT OF AN OBSTRUCTED NATURAL CANAL

BACKGROUND OF THE INVENTION

The present invention relates to the therapeutic treatment, by means other than surgical or medicinal means, of a natural canal of the human or animal body, such as a natural passage or a lumen, through which a fluid is passed or flows, in particular a bodily fluid, and whose passage becomes narrowed, or subject to a stenosis or obstruction.

More precisely, the invention relates to the treatment of a natural canal as defined previously, delimited by a living wall, for example a mucous membrane, which is obstructed or whose cross-section becomes narrowed or limited, locally or over the length of the said canal, under the effect of the centripetal compression exerted by a hypertrophic extrinsic tissue. By way of example of such natural canals, mention may be made of the urinary, digestive, gynecological, etc. passages, excluding the upper airways, and by way of examples of such hypertrophic external tissues, mention may be made of malignant and benign tumors of an organ or gland surrounding the said canal.

According to the invention, the term treatment is to be taken to mean intervention on the natural canal, of the physical and/or mechanical type, aimed at restoring the flow in the said canal.

The present invention is now introduced, defined and expanded on with reference to the treatment of obstruction of the prostatic urethra which is due to a benign prostatic hypertrophy (abbreviated to BPH), it being understood that this is one application of the present invention amongst many others. In this particular case, and referring to the general definition given previously, the natural canal is the entirety of the prostatic segment of the urethra, above the sphincter as far as the neck of the urinary bladder, and the periurethral hypertrophic external tissue consists of the benign prostatic adenoma; this adenoma is an adenomyofibroma comprising a glandular, smooth muscle component and connective tissue.

Currently, it is known to treat BPH by thermotherapy, and for this purpose, benign adenoma is selectively destroyed or reduced, by introducing within it or in situ a controlled dose of thermal treatment energy in order to necrose at least part of the adenoma.

"Thermal treatment energy", in the sense of the present description or invention, means both supply of heat, at a therapeutic temperature, for example lying between 45° and 100° C. and supply of cold, at low temperature, for example of the cryogenic type.

And preferably, the dose of thermal treatment energy is introduced selectively within the benign adenoma, via the endocavitary, that is to say endourethral, route by introduction into the urethra of a microwave radiation source, and whilst simultaneously preserving the urethral mucous membrane, by superficial conductive cooling. This technique is now well known under the name of transurethral microwave therapy (abbreviated to TUMT) and can be implemented with various types of equipment available on the market, for example the equipment of the trademark PROSTATRON, sold by the company Technomed International Inc based at Northwoods Business Park, 100 Rosewood Drive, Danvers, Mass. 01930, USA.

This therapy has a tissue effect: the prolonged exposure of the adenomatous tissue at high temperature is responsible for a coagulation necrosis. The obstruction or rupture of the small vessels in the zone treated by the heat is responsible for a prostatic infarction whose starting point is a peripheral thrombosis of the blood capillaries. Macroscopic examination of the coagulated tissue zone shows a thermal lesion which may extend in depth over more than 10 mm from the lumen of the urethra. In contrast, the surface mucosa and submucosa of the urethra are not destroyed because they have been protected during the treatment, over a depth of 2 to 3 mm, by the cooling circuit. Microscopic examination of the microwave thermal lesion shows a destruction of the cells forming the adenoma.

At the clinical level, the improvement in the disorders of the patient has a twofold explanation:

the probable destruction of the neurological receptors responsible for the voiding reflex between the prostatic urethra and the bladder muscle (detrusor); the consequence is, amongst other symptoms, a decrease in the frequency voiding by day and night; this is the therapeutic effect sought by the patient and his doctor the decrease in the pressure exerted by the adenoma on the urethra: the consequence is an improvement in the urine flow with an improvement of the emptying of the urinary bladder.

This being the case, this therapy has various drawbacks which should be explained.

It causes the rapid appearance of an interstitial edema. It forms in a few hours; it is responsible for an expansion of the adenomatous tissue treated, towards the lumen of the urethra. The edema increases the pressure at the urethra, decreases the urine flow and may be responsible for the occurrence of acute urinary retention. This edema has the consequence, in chronological order:

of a risk of acute urinary retention; the acute urinary retention requires urgent drainage by insertion of a urethral catheter (Foley catheter) or of a suprapubic catheter; the urine is then continuously collected in a collection bag, which represents a significant handicap for the quality of life; the drain is left in place for a few days to several weeks.

a temporary worsening of the urinary disorders, of the order of one to several weeks.

Healing of the lesion generated by the necrosis may occur in the centripetal direction, over several months, in a more or less disordered manner, and possibly in the wrong position, namely with the urethral lumen partially or completely closed, which can completely or partially negate the benefit of TUMT.

The present invention has the general object of overcoming the traditional drawbacks of thermotherapy, whatever the technique used.

The object of the present invention is to increase the efficiency of thermotherapy techniques, whilst decreasing their morbidity.

A further object of the invention is to increase the lumen of the natural canal, until values are obtained of the same order as those obtained by a conventional or endoscopic surgical operation directly on the hypertrophic extrinsic tissue.

Another object of the invention is to shorten the delay of the onset of the therapeutic benefit, since an increase in the lumen of the previously obstructed natural canal can be obtained almost immediately.

A final object of the invention is to decrease the rate of morbidity in thermotherapy in general, for example due to the rapid onset of an edema.

SUMMARY OF THE INVENTION

According to the present invention, and in succession:

(a) the extrinsic tissue is selectively damaged, by introducing within it a controlled dose of treatment energy in order to necrose at least a part of the said tissue; the treatment energy is ionizing, for example radiotherapy, or non-ionizing and thermal;

(b) there is fitted into the said natural canal, immediately after or shortly after step (a), a prosthesis, expandable or non-expandable, comprising a tubular element biologically compatible with the mucous membrane, exerting on the latter a centrifugal compression, and optionally imparting a posture, with deformation, and defining an open and permanent passage in the said natural canal;

(c) the extrinsic tissue is left to heal on and around the prosthesis;

(d) after healing of the extrinsic tissue, the prosthesis is extracted from the natural canal, whilst obtaining in the latter a definitive passage modeled on the external dimensions and possibly the shape of the said prosthesis.

The present invention essentially combines synergetically and sequentially, on the one hand traditional thermotherapy, combining coagulating heating or cooling of the hypertrophic extrinsic tissue with the action of the removable, preferably self-immobilizing, anatomical and non-traumatizing tubular prosthesis which promotes centrifugal healing.

As regards thermotherapy which can be used according to the invention, reference will be made to U.S. patent application Ser. No. 438,741, of 17 Nov. 1989, and to European Document No. EP-A-0,370,890, the content of which is integrated in the present description, as required.

As regards a prosthesis which can be used according to the invention, reference will be made to French Patent Application No. 93 02284 of 19 Feb. 1993, the content of which is integrated in the present description as required.

The present invention leads to a novel concept of therapeutic treatment of an obstructed natural canal: thermal modelling or thermoplasty which results sequentially from the thermotherapy by a physical agent responsible for tissue coagulation, and, on the other hand, the fitting of an intracavitary prosthesis responsible for pushing back the coagulated tissue by centrifugal mechanical pressure exerted on the coagulated tissue.

In the thermotherapy-prosthesis sense, there is a synergy: the thermotherapy weakens the tissue responsible for the obstruction by coagulating it, and facilitates the mechanical action of the prosthesis which deforms the weakened tissue.

In the prosthesis-thermotherapy sense, there is also a synergy: the prosthesis completes and amplifies the effect of the irradiation. In fact, on the one hand, the mechanical pressure which the prosthesis exerts on the vascularization of the obstructing tissue accentuates the effect of intravascular coagulation previously caused by the heat, and, on the other hand, the prosthesis amplifies the retraction of the tissue coagulated by the heat, and directs its healing along a shape adapted to reduction of the obstacle.

Finally, the prosthesis acts as a mold for the natural canal. The healing will take place in the centrifugal direction. The mold serves to direct the healing around the shape of the prosthesis. At the end of the healing, and after withdrawal of the prosthesis, the natural canal keeps an open shape, for example that of a tube which has retained its elasticity. In the case of the urethra, with a full urinary bladder, the lumen is open, which facilitates micturition; with an empty urinary bladder, the tube may be collapsed and thus possibly allow the preservation of normal antegrade ejaculation.

According to a preferred embodiment of the invention, the dose of thermal treatment energy is introduced during step a) defined hereinabove, within the extrinsic tissue, via at least any one of the routes chosen from the group comprising the endocavitary route, the interstitial route and the extracorporeal route, with at least any one of the heat sources chosen from the group comprising:

an emission of microwave radiation
an emission of ultrasound, focused on the extrinsic tissue
an emission of laser radiation
an emission of ultrashort, elastic radio waves
an agent for nuclear magnetic resonance of the extrinsic tissue
and a cryogenic source.

Preferably, during step (a), the living wall of the natural canal is preserved, by supplying it, by conduction, with another thermal energy which counteracts the effects of the dose of thermal treatment energy which are harmful for the said wall.

By way of example, but not exclusively, during step (a) the dose of thermal treatment energy is supplied by the endocavitary route, with a source emitting microwave radiation, and the living wall of the natural canal is preserved, by cooling it by conduction, for example in surface contact with the said wall.

DESCRIPTION OF PREFERRED EMBODIMENTS

The present invention is now described with reference to the attached drawing, in which FIGS. 1 to 5 schematically and successively represent the various steps in the therapeutic treatment method according to the invention.

Figure 1:
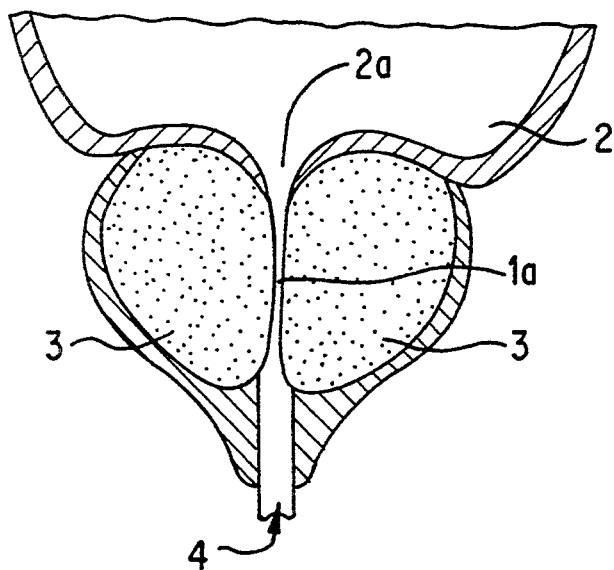
FIGS. 1–5 schematically represent the therapeutic treatment method according to the invention.

According to FIG. 1, the prostatic segment of the urethra, constituting a natural canal in the sense of the invention, has been represented diagrammatically, under the numerical reference 1. This segment emerges at the top through the neck 2a of the urinary bladder into the urinary bladder 2. A benign prostatic adenoma 3, constituting hypertrophic extrinsic tissue in the sense of the invention, compresses the urethra inward, so that the latter is partially obstructed, as represented by the reference 1a.

Figure 2:
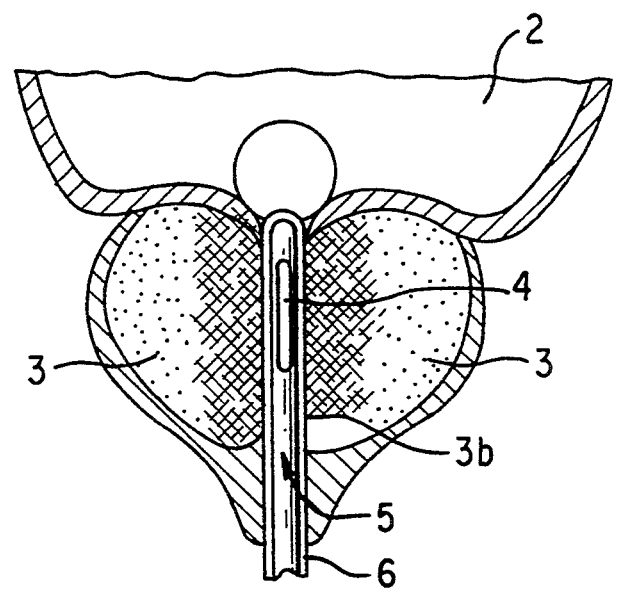

According to FIG. 2, and according to the first step (a) of the method according to the invention, there is introduced into the prostatic segment 1 a miniaturized catheter 5 which integrates, on the one hand, an antenna 4 emitting microwave radiation, and, on the other hand, a surface cooling circuit 6, the whole belonging to equipment as defined previously, that is to say for example an apparatus of the trademark PROSTATRON, sold by the company Technomed International Inc.

During this step, under the effect of the microwave radiation, neutralized at the level of the mucous membrane of the urethra, but acting selectively on the prostate 3, the adenoma of the latter is reduced, by introducing within the prostate a dose of thermal treatment energy which is carefully controlled in order to necrose a large part 3b of the hypertrophic tissue, at least in immediate proximity to the urethra. And the catheter 5 is extracted.

Figure 3:
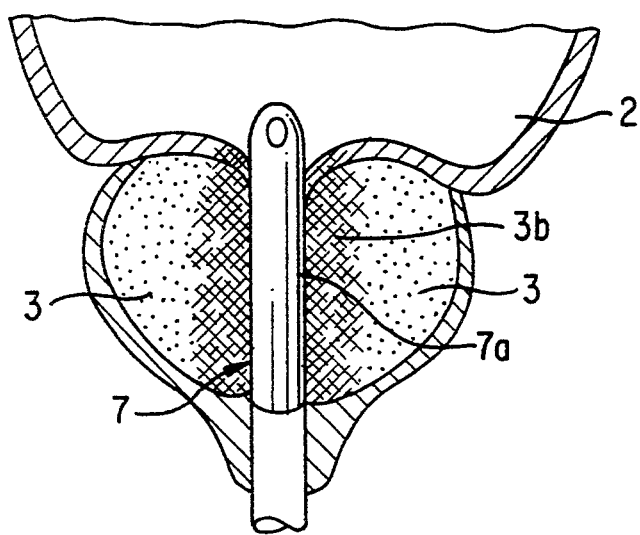

According to FIG. 3, and according to the second step (b), there is fitted into the urethra segment 1, immediately or shortly after step (a) a prosthesis 7, essentially consisting of a tubular element, expandable or non-expandable, biologically compatible with the mucous membrane, exerting on the latter a centrifugal compression or deformation, with a posture. Such prostheses are well known in the state of the art, for example for promoting flow of urine, and are preferably self-immobilizing, anatomical and non-traumatizing. The fitted prosthesis 7 defines an open and permanent passage 7a in the urethral segment 1.

Figure 4:
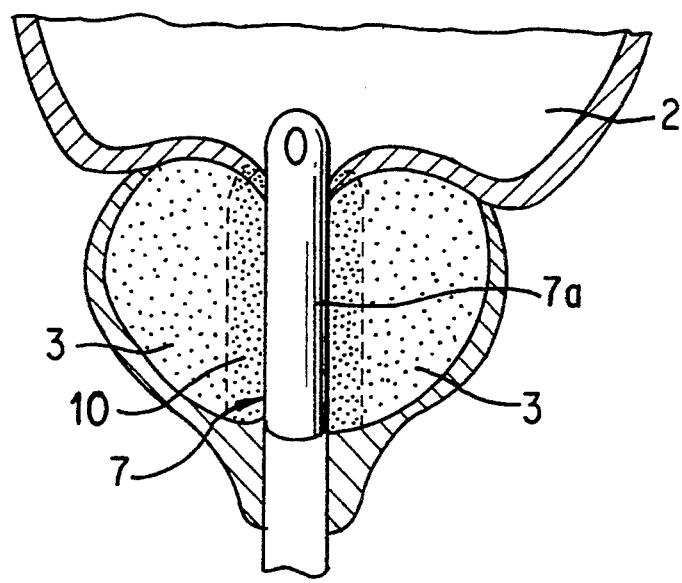

According to FIG. 4, and according to step (c), the prostatic tissue is allowed to heal, obtaining a tube of fibrosis 10, replacing the tissue damaged at this location.

Figure 5:
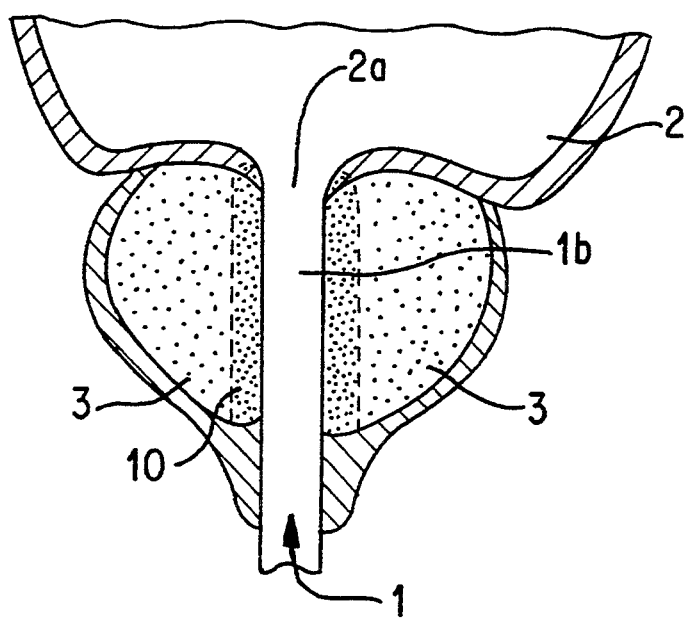

According to FIG. 5, and after a few months, and according to step (d) of the method according to the invention, after healing of the prostatic tissue, the prosthesis 7 is extracted from the prostatic segment 1, obtaining in the latter a definitive passage 1b modelled on the external dimensions of the prosthesis.

Twenty patients were treated for a urinary obstacle linked with a benign prostatic hypertrophy according to the principle of thermal modelling or thermoplasty described previously.

The treatment included a session of conventional microwave thermotherapy, immediately followed after withdrawal of the urethral treatment catheter by the fitting of a temporary self-immobilizing endourethral prosthesis left in place for eight weeks.

The insertion of the prosthesis (immediately or shortly after the thermotherapy session) presents no particular difficulty, compared to fitting in a patient who has not been previously treated.

Micturition is obtained immediately and no retention was observed.

The immediate (first week) and medium-term (during the first two months) tolerance is close to that observed in patients treated simply by thermotherapy, without urinary draining. The comfort of the patient would be even better in the group wearing a prosthesis, despite the presence of a foreign body in the urethra. No infection, no hematuria or urethral bleeding is noted. The patients who are sexually active noted the appearance of retrograde ejaculation.

The improvement in the symptoms after thermal modelling is close to that observed with simple thermotherapy (reduction in the score of the symptoms of the order of 70%).

In contrast, after thermal modelling, the improvement in the urine flow is much more marked. The first patients, five in number, from which the prosthesis was removed at the end of two months, have, at the time of evaluation at the third month (that is to say one month after removal of the prosthesis), an increase in the urine flow markedly greater than that observed after thermotherapy alone. The improvement in the delivery urine flow is multiplied by two; it passes from an average improvement of 35% after simple thermotherapy to 70% or more after thermal modelling.

Radiological exploration, three months after thermal modelling shows a wide opening in the prostatic urethra during micturition (tubular or conical shape), whereas the urethra is filiform at the moment of retrograde filling of the urinary bladder.

The twofold multiplication in the result on the urine flow and the observation of a cavity of tubular or conical shape at the moment of micturition are two new results which demonstrate the effectiveness of thermal modelling according to the invention; in fact, these two observations do not exist, or only exceptionally exist, after conventional thermotherapy. These results demonstrate the advantage of the therapeutic treatment according to the invention.

I claim:

1. Method for therapeutic treatment of a natural canal of a human or animal body for passage of fluid, delimited by a living wall, and whose passage undergoes a stenosis or is obstructed by centripetal compression exerted by a hypertrophic extrinsic tissue, comprising:
   (a) selectively damaging the extrinsic tissue by introducing within it a controlled dose of ionizing or non-ionizing treatment energy in order to necrose at least a part of said tissue;
   (b) fitting a prosthesis into said natural canal, immediately after step (a), said prosthesis comprising a tubular element biologically compatible with the wall, exerting on the wall a centrifugal compression, and optionally imparting a posture, and defining an open and permanent passage in said canal;
   (c) permitting the extrinsic tissue to heal on and around the prosthesis; and
   (d) after healing of the extrinsic tissue, extracting the prosthesis from the natural canal to obtain in the canal a definitive passage modeled on a external dimension of said prosthesis.

2. Method according to claim 1, wherein step a) includes introducing a dose of non-ionizing thermal treatment energy is introduced during step a) within the extrinsic tissue, via at least any one of the routes chosen from the group consisting the endocavitary route, the interstitial route and the extracorporeal route, with a heat source of at least any one chosen from the group consisting of:
   an emission of microwave radiation
   an emission of ultrasound, focused on the extrinsic tissue
   an emission of laser radiation
   an emission of ultrashort, elastic waves generated by piezoelectricity
   an agent for nuclear magnetic resonance of the extrinsic tissue
   and a cryogenic source.

3. Method according to claim 2, wherein step a) includes preserving at least a part of the wall of the natural canal by supplying it, by conduction, with another thermal energy which counteracts the effects of the dose of thermal treatment energy which are harmful for the said wall.

4. Method according to claim 3, wherein step a) includes supplying said dose of non-ionizing thermal treatment energy by the endocavitary route, with a source emitting microwave radiation, and at least part of the wall of the natural canal is preserved, by cooling it by conduction.

5. Method according to claim 1, according to which the treatment energy is non-ionizing and thermal.

6. Method according to claim 1, including the step of obtaining the treatment energy, which is ionizing, and is obtained by a radiotherapy source.

7. Method according to claim 1, according to which the natural canal is the prostatic segment of a urethra, and the hypertrophic extrinsic tissue is a benign prostatic adenoma.

8. Method according to claim 1, wherein said living wall comprises a mucous membrane.

9. Method according to claim 1, wherein said fluid is a bodily fluid.

* * * * *